(12) United States Patent
Main

(10) Patent No.: US 6,554,161 B2
(45) Date of Patent: Apr. 29, 2003

(54) MULTI-BARREL DISPENSING APPARATUS

(75) Inventor: John Robert Main, Hamilton (NZ)

(73) Assignee: Prima Technologies Limited, Hamilton (NZ)

( * ) Notice: Subject to any disclaimer, the term of this patent is extended or adjusted under 35 U.S.C. 154(b) by 0 days.

(21) Appl. No.: 09/811,633

(22) Filed: Mar. 20, 2001

(65) Prior Publication Data

US 2002/0011501 A1 Jan. 31, 2002

(30) Foreign Application Priority Data

Mar. 21, 2000 (NZ) ................................ 503496

(51) Int. Cl.⁷ ................................................ B67D 5/22
(52) U.S. Cl. ...................... 222/43; 222/287; 222/309; 128/223
(58) Field of Search ............................. 222/41, 43, 47, 222/309, 287; 128/223, 235

(56) References Cited

U.S. PATENT DOCUMENTS 2,750,943 A * 6/1956 Dann ........................... 604/223
4,033,346 A * 7/1977 Phillips et al. ............... 604/186
4,526,294 A * 7/1985 Hirschmann et al. ........ 222/309
5,988,452 A * 11/1999 Dent et al. ................... 222/309

FOREIGN PATENT DOCUMENTS

NZ 191016 11/1981
NZ 222692 10/1989

* cited by examiner

Primary Examiner—Gene Mancene
Assistant Examiner—Melvin Cartagena
(74) Attorney, Agent, or Firm—Jacobson Holman PLLC

(57) ABSTRACT

A dispensing apparatus for a liquid which relies on molded components capable of being interchanged to provide, in addition to incremental adjustment within a range of dosages allowed by stroke limiting rotational adjustment of the relativity of escarpment and abutment members, the change of one or both the spread of the dosage range and at least one limit of the range.

27 Claims, 16 Drawing Sheets

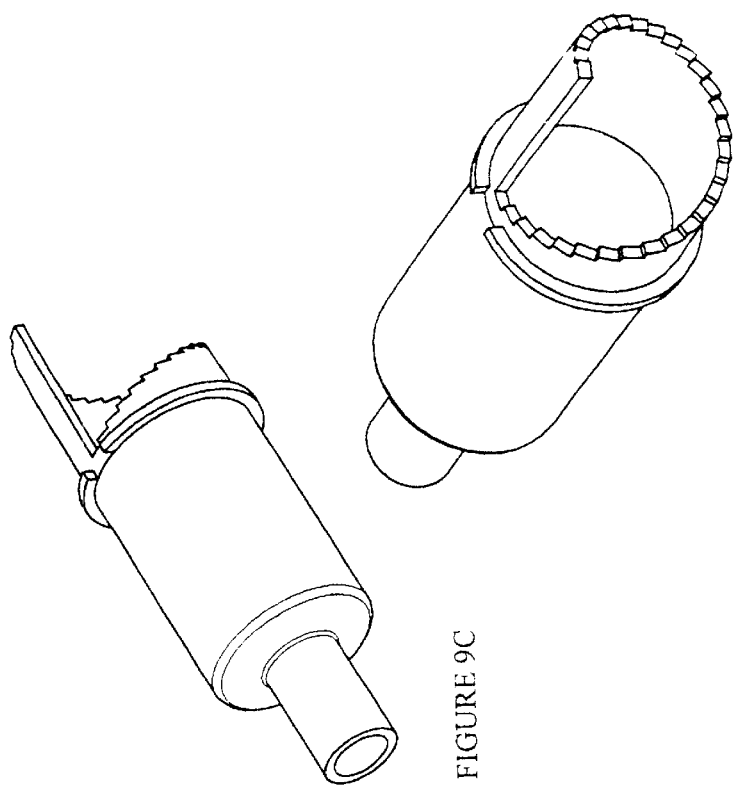
FIGURE 9D
FIGURE 9C
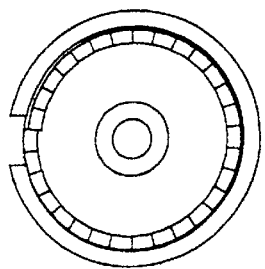
FIGURE 9E
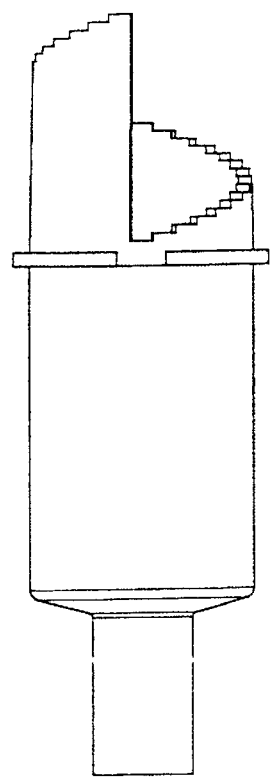
FIGURE 9A
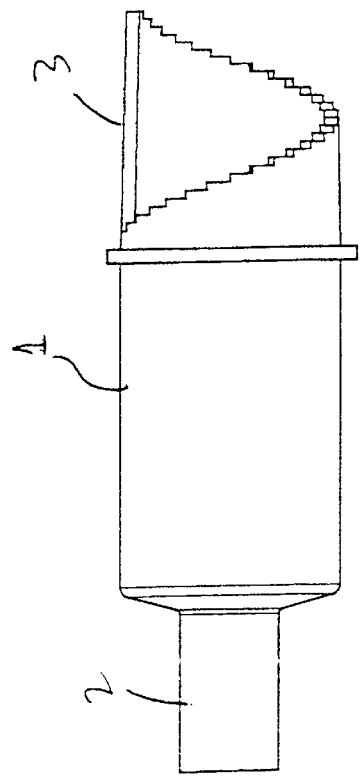
FIGURE 9B

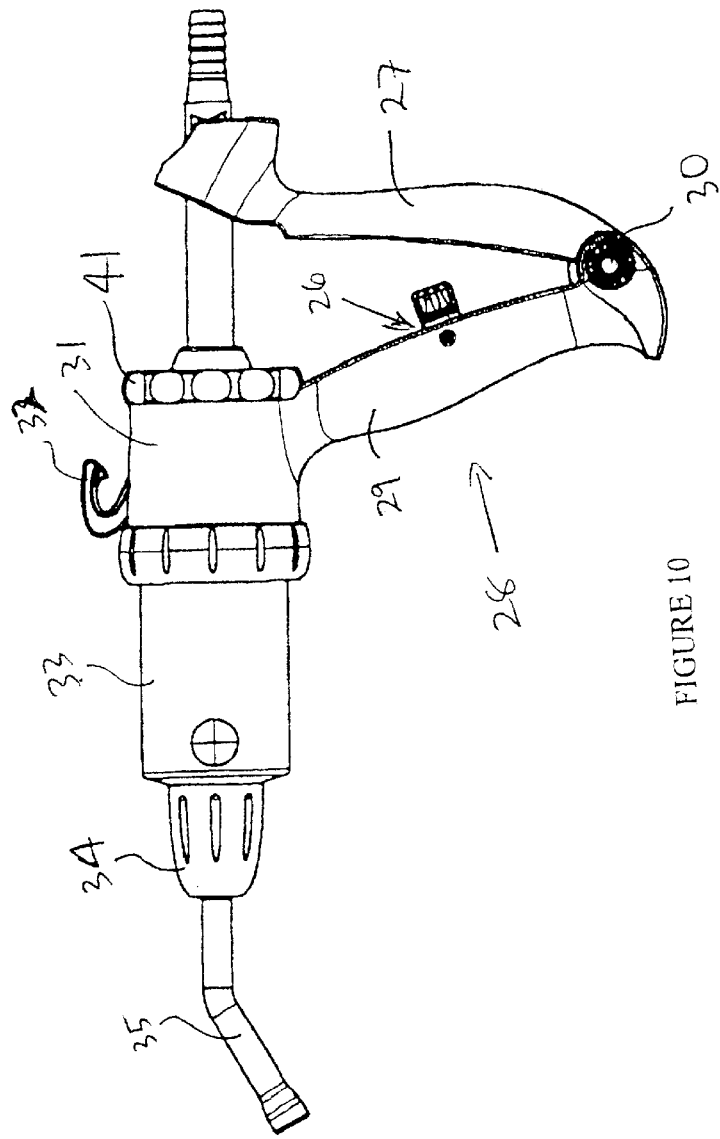
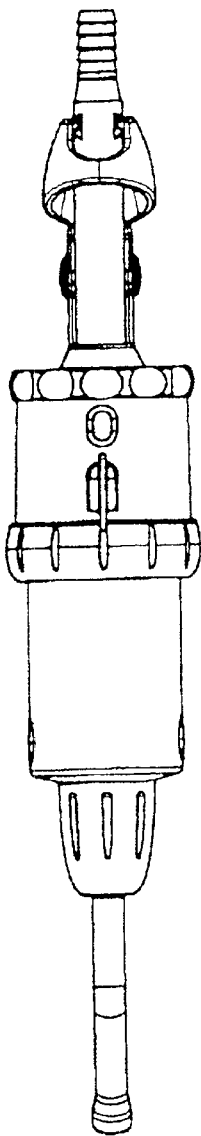
FIGURE 10
FIGURE 11
FIGURE 12
FIGURE 13

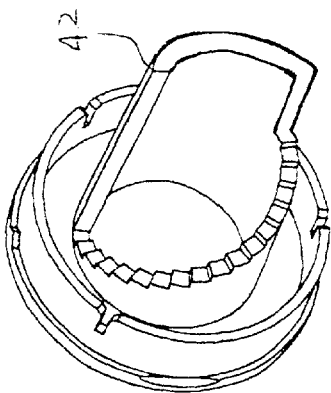
FIGURE 17D
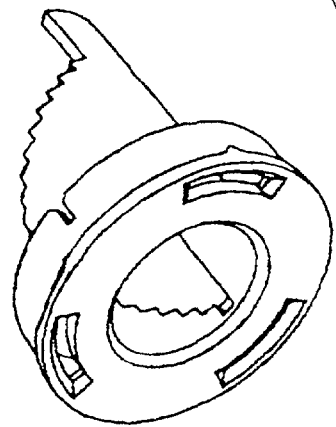
FIGURE 17C
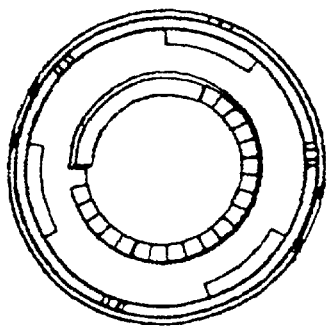
FIGURE 17E
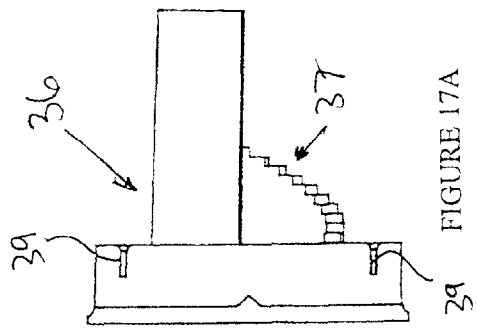
FIGURE 17A FIGURE 17B
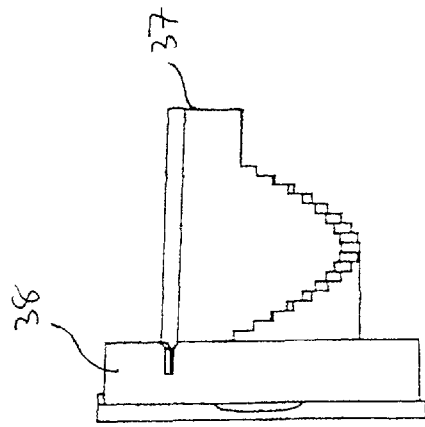
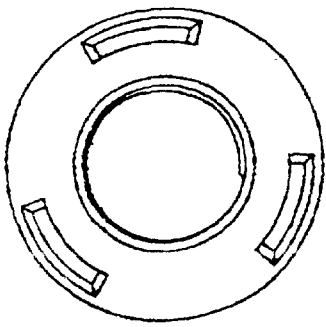
FIGURE 17F

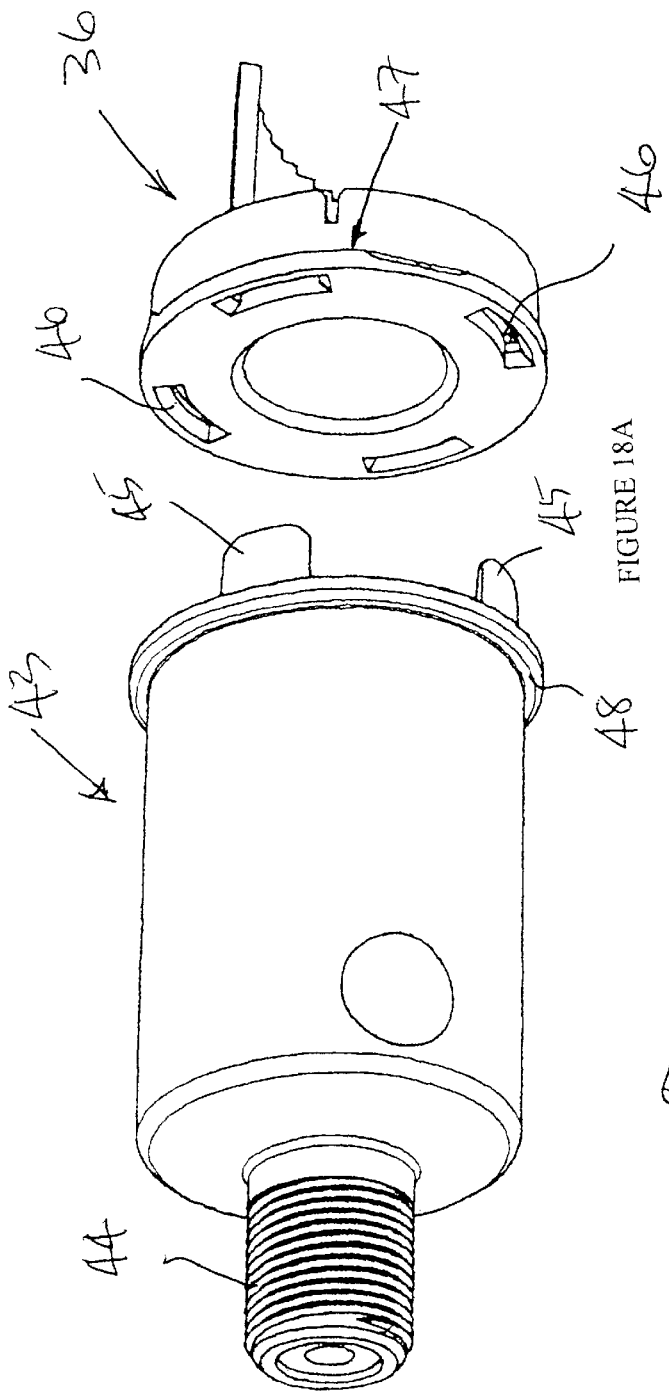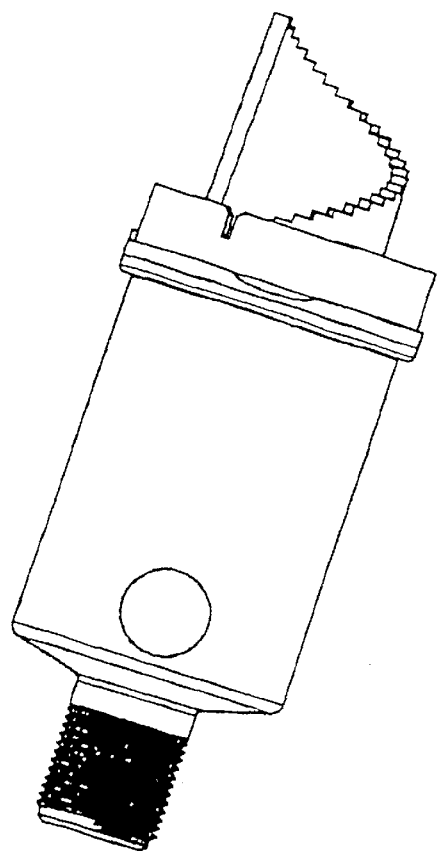
FIGURE 18A
FIGURE 18B

MULTI-BARREL DISPENSING APPARATUS

TECHNICAL BACKGROUND

The present invention relates to dispensing apparatus.

BACKGROUND ART

Dispensing apparatus of a kind for dispensing a fluid (usually a viscous liquid, whether in the form of a paste or otherwise) is well known for applying therapeutic substances into animals or onto animals. Such dispensing apparatus also have applications elsewhere, e.g.; for dispensing predetermined amounts of a material into, for example, a pot or the like for growing plants.

Dispensing apparatus of the present invention is preferably of a kind adapted for oral drenching or pour-on application of an animal remedy and/or supplement. Examples include parasiticides such as anthelmintics.

Whilst discharging of such fluids has been common from cartridges it is more usual for such liquid or liquid carried materials to be supplied via a conduit from a tank or pouch pack into a dispensing gun type apparatus. In the preferred form of the present invention that is the form of dispensing apparatus to which the present invention is directed. Accordingly, references to an "outlet" should be taken to include within its scope any downstream device to assist (whether with or without the use of additional valving) the application of the fluid to a desired animal location.

There is sometimes a desire to be able to control the level of dose. The present invention relates to such apparatus having a capability of allowing a chosen dose within a range of doses. Devices of this kind have hitherto been known.

One such dose adjustment mechanism involves a rotational adjustor. Such a form of dispensing apparatus is disclosed in New Zealand Patent Specification No. 191016 of N J Phillips Pty. Limited and the full content thereof is hereby here included by way of reference.

Another form of such apparatus is that disclosed in New Zealand Patent Specification No. 222692 of Instrument Supplies Limited. It disclosed the use of a rotatable adjustor which carries a semi-circular wall having at each end of the wall edges that extend mutually parallel from the rotatable knob which provides the wall base. Such a wall between the first and second edges has its free periphery stepped so as to act on a fixed abutment member in the drench gun, the step aligned determining the axial extent of piston movement with the stepped semi-circular wall.

DISCLOSURE OF THE INVENTION

The present invention is directed to an alternative to such prior art devices.

As used herein "liquid" covers solutions, suspensions, emulsions, suspo-emulsions, gels, etc. capable of being piston expressed from an outlet.

In a first aspect the present invention consists in dispensing apparatus of a kind having a barrel with an inlet and an outlet and an operator actuable piston reciprocally movable in said barrel, wherein said piston, in use, when moving away from said outlet, allows a liquid to enter space between said piston and said outlet, and wherein subsequent movement ("discharging movement") of said piston, in use, towards said outlet causes liquid to exit said outlet, and wherein the stroke of said discharging movement is controlled by a stop mechanism for the piston, said stop mechanism comprising including spiral staircase means through which liquid can pass and a staircase step abutment member carried by the piston or an assembly which includes the piston can butt at the limit of said discharging movement on a step of said spiral staircase means, said abutment member being rotatable about both the barrel and spiral staircase axes by externally accessible means to determine a stroke limiting choice of step in the staircase to encounter the abutment member and thus the quantity of liquid to be dispensed by a single discharging movement of said piston.

In another aspect the present invention consists in liquid dispensing apparatus having hand actuable means to move a piston against biassing means so as to discharge at least part of the liquid content from a barrel, said barrel having fixed relative thereto a helical abutment structure and wherein said piston forms part of an assembly which allows an uptake of liquid into said barrel during retraction under the action of said biassing means and wherein the limit of the liquid discharging step from that retracted piston condition is determined by the selection of that part of the helical abutment feature to be encountered during the dispensing stroke.

Preferably said helical abutment feature is a staircase. In other forms it can be a continuous surface.

Preferably one or more of the barrel, piston and helical abutment structure is detachable from the other components of the apparatus.

In another aspect the present invention consists in, in a drench gun (whether for pour-on or oral drenching purposes or for any other purpose) of a kind capable of being actuated to cause a piston to reciprocate within a dispensing channel, there being one way valve means to allow an uptake of liquid to be dispensed into the dispensing side of the piston in the barrel, a stroke adjustment mechanism comprising or including an abutment member carried by the piston assembly capable of being rotated about the piston axis by means of an adjustment accessible to an operator (such adjustment preferably being possible by hand with reference to a scale indicating the quantity to be dispensed) and a helical abutment feature (stepped or continuous or otherwise) adapted to provide an abutment for said rotatable abutment member thereby to adjust the allowed extent of travel of the piston during a dispensing motion owing to the end of travel occurrence of an abutment between the piston carried abutment feature and the helical abutment feature.

Preferably said helical abutment feature is a moulded element (preferably in the form of a spiral staircase or the like member) that is integral with or which is fixed in a fabricated structure relative to the barrel or that part of the barrel to be a sleeve for the piston.

Preferably said helical abutment feature is or defines a spiral staircase.

Preferably the said piston includes an axial conduit controlled by said one way valve means.

Preferably said piston is biassed to a retracted condition.

Preferably said piston is biassed by means included in the handle structure.

Preferably said handle is squeezed against the bias of said biassing means to cause a liquid dispensing stroke of said piston is capable of being squeezed to confer a withdrawing bias to the assembly.

Preferably said drench gun is disassemblable to enable removal of a barrel, a piston and/or a helical abutment feature.

Preferably said drench gun is capable of reassembly after disassembly with the same or a different barrel, piston and/or helical abutment feature.

In a further aspect the present invention consists in an apparatus for dispensing a selected volume of a liquid, said apparatus comprising or including:

- a handle assembly of pivotally interconnected first and second handle components and means to bias such handle components apart about the pivot, one of said components ("the first component") at a region distal from said pivot having a sleeve form, the axis of which sleeve form is normal to said pivot axis,
- a piston assembly linked from the second handle component at or from a region distal thereof from said pivot, such piston assembly extending through said sleeve, said piston assembly connecting said second component to the piston and providing or defining a conduit for the receiving and conveying liquid to be dispensed via a one way valve out of said piston,
- a member or assembly (thereafter "abutment defining member") located on or about said piston assembly and rotatable about the stroke axis thereof by manual actuation externally of said sleeve,
- an escarpment member located at least in part in said sleeve and providing an escarpment of steps on each of at least several of which part of said abutment defining member can abut to limit the discharge stroke of said piston assembly upon a manual squeezing of the handle components together about the pivot, and
- a barrel member about the piston adjacent to and/or indexed to the sleeve of said first component and/or said escarpment member and held in a fixed relationship with both the sleeve and the escarpment member, said barrel member having an outlet, a one way valved outlet or extending to a one way valved outlet assembly,
- wherein, reliant on the one way of valve of said piston assembly, liquid can enter said barrel between said piston and outlet at least as said second handled component retracts under the action of said means to bias and thereafter the piston can drive liquid from the barrel to the extent allowed by the discharge stroke limit of the piston in the barrel as the handle components are squeezed against the bias, such stroke limit being determined by the particular alignment of the abutment defining member with a particular step of the escarpment member.

Preferably said barrel member is held in said fixed relationship with the sleeve and escarpment member by a screw engaged collar engaged to said sleeve.

Preferably said barrel member indexes to said escarpment member by a male/female inter-engagement.

Preferably said escarpment member is in the form of a spiral staircase formed as part of a moulded member having an outwardly extending flange to butt on one end of said sleeve of said first component and an inwardly extending flange having openings each to receive a projection of said barrel in said male/female indexing manner.

In still a further aspect the present invention consists in an apparatus for dispensing a selected volume of a liquid, said apparatus comprising or including

- a handle assembly of first and second handle components inter-related sufficiently to ensure the prospect of reproducible movement towards or away from each other,
- an assembly supported on one of said handle components ("the first component") which comprises or includes
  - an escarpment member which defines a spiral staircase that faces back towards the second handle component and
  - a barrel coaxially aligned with said escarpment member, said barrel having or extending to an outlet, and
- an assembly including or comprising a conduit capable of being connected to a source of liquid supply which assembly extends from said second handle component into said barrel where it carries a piston, there being a one way valve in the conduit and/or piston to enable liquid entry upon retraction of the piston,
- and wherein the conduit carries there around an abutment member associated with an external rotational control which can be aligned with a desired step of the escarpment member spiral staircase so as to be determinate of the dispensing stroke limit of the piston.

In a further aspect the present invention consists in an apparatus for dispensing a selected volume of a liquid, said apparatus comprising or including:

- a handle assembly of pivotally interconnected first and second handle components and means to bias such handle components apart about the pivot, one of said components ("the first component") at a region distal from said pivot having a sleeve form, the axis of which sleeve form is normal to said pivot axis;
- a piston assembly linked from the second handle component at or from a region distal thereof from said pivot, such piston assembly extending through said sleeve, said piston assembly connecting said second component to an interchangeable piston and providing or defining a conduit for the receiving and conveying liquid to be dispensed via a one way valve out of said piston;
- a member or assembly (thereafter "abutment defining member") located on or about said piston assembly and rotatable about the stroke axis thereof by manual actuation externally of said sleeve;
- an interchangeable escarpment member located at least in part in said sleeve and providing an escarpment of steps on each of at least of several of which part of said abutment defining member can abut to limit the discharge stroke of said piston assembly upon a manual squeezing of the handle components together about the pivot; and
- an interchangeable barrel member about the piston adjacent to and/or indexed to the sleeve of said first component and/or said escarpment member and held in a fixed relationship with both the sleeve and the escarpment member, said barrel member having an outlet, a one way valved outlet or extending to a one way valved outlet assembly;
- wherein, reliant on the one way of valve of said piston assembly, liquid can enter said barrel between said piston and outlet at least as said second handled component retracts under the action of said means to bias and thereafter the piston can drive liquid from the barrel to the extent allowed by the discharge stroke limit of the piston in the barrel as the handle components are squeezed against the bias, such stroke limit being determined by the particular alignment of the abutment defining member with a particular step of the escarpment member,
- and wherein interchange of at least one of the interchangeable members can vary the range of volumes capable of being dispensed.

Preferably both the piston and its barrel is interchangeable.

In a further aspect the present inventions consists in an apparatus for dispensing a selected volume of a liquid, said apparatus comprising or including a handle assembly of first and second handle components inter-related sufficiently to ensure the prospect of reproducible movement towards or away from each other;

an assembly supported by one of said handle components ("the first component") which includes an interchangeable barrel having or extending to an outlet; and an assembly including or comprising a conduit capable of being connected to a source of liquid supply which assembly extends from said second handle component into said barrel where it carries an interchangeable piston appropriate for the barrel selected, there being a one way valve in the conduit and/or piston to enable liquid entry upon retraction of the piston; and an interacting arrangement of an abutment member and an escarpment member capable of being interactive to limit a stroke of said piston in said barrel, yet by rotation of the members relative to each other can vary that stroke;

and wherein volume can in addition be varied by at least one of
  (a) barrel interchange,
  (b) piston interchange,
  (c) escarpment member interchange, and
  (d) abutment member interchange.

Preferably in use, said apparatus can dispense incrementally over a fist range and, after reassembly with associated components, can dispense incrementally over a second range not coextensive with said first range.

In another aspect the present invention consists in (I) apparatus for dispensing a selected volume of a liquid, said apparatus comprising or including:

a handle assembly of pivotally interconnected first and second handle components and means to bias such handle components apart about the pivot, one of said components ("the first component") at a region distal from said pivot having a sleeve form, the axis of which sleeve form is normal to said pivot axis;

a piston assembly linked from the second handle component at or from a region distal thereof from said pivot, such piston assembly extending through said sleeve, said piston assembly connecting said second component to an interchangeable piston and providing or defining a conduit for the receiving and conveying of liquid to be dispensed via a one way valve out of said piston;

a member or assembly (thereafter "abutment defining member") located on or about said piston assembly and rotatable about the stroke axis thereof by manual actuation externally of said sleeve;

an interchangeable escarpment member located at least in part in said sleeve and providing an escarpment of steps on each of at least of several of which part of said abutment defining member can abut to limit the discharge stroke of said piston assembly upon a manual squeezing of the handle components together about the pivot; and an interchangeable barrel member about the piston adjacent to and/or indexed to the sleeve of said first component and/or said escarpment member and held in a fixed relationship with both the sleeve and the escarpment member, said barrel member having an outlet, a one way valved outlet or extending to a one way valved outlet assembly;

wherein, reliant on the one way valve of said piston assembly, liquid can enter said barrel between said piston and outlet at least as said second handled component retracts under the action of said means to bias and thereafter the piston can drive liquid from the barrel to the extent allowed by the discharge stroke limit of the piston in the barrel as the handle components are squeezed against the bias, such stroke limit being determined by the particular alignment of the abutment defining member with a particular step of the escarpment member, and wherein interchange of at least one of the interchangeable members can vary the range of volumes capable of being dispensed, and (II) at least one or more of said interchangeable members the use of which in the apparatus will lead to a dosage range not coextensive with the dosage range of the apparatus in its initial form or when assembled as in (I).

In another aspect the present invention consists in (I) apparatus for dispensing a selected volume of a liquid, said apparatus comprising or including a handle assembly of first and second handle components inter-related sufficiently to ensure the prospect of reproducible movement towards or away from each other;

an assembly supported by one of said handle components ("the first component") which includes an interchangeable barrel having or extending to an outlet; and an assembly including or comprising a conduit capable of being connected to a source of liquid supply which assembly extends from said second handle component into said barrel where it carries an interchangeable piston appropriate for the barrel selected, there being a one way valve in the conduit and/or piston to enable liquid entry upon retraction of the piston; and an interacting arrangement of an abutment member and an escarpment member capable of being interactive to limit a stroke of said piston in said barrel, yet by rotation of the members relative to each other can vary that stroke;

and wherein volume can in addition be varied by at least one of
  (a) barrel interchange,
  (b) piston interchange,
  (c) escarpment member interchange, and
  (d) abutment member interchange, and (II) at least one or more additional components to allow (a), (b), (c) and/or (d).

In a further aspect the present invention consists in a method of varying the range of incremental dosages capable of being dispensed from a dispensing apparatus which comprises taking a combination as previously defined and varying the discharge volume allowed for a particular stroke limit by component interchange.

In a further aspect the present invention consists in a method of dispensing a range of selected dosages within a range or within ranges which involved the operative use of the apparatus as herein described.

Preferably the apparatus is as herein described where any one or more of any component is substantially hereinafter described with reference to any one or more of the accompanying drawings.

Preferably the method of dispensing a liquid over increments in one or more ranges is performed substantially herein described with reference to any one or more of the accompanying drawings.

Preferably the arrangement is substantially as hereinafter described with reference to any of the accompanying drawings.

In another aspect the invention consists in the use of the apparatus as herein described.

As used herein reference to "helical" includes any similar such arrangement which presents some degree of spiral arrangement continuous or discontinuous, ie; it could be castellations carried internally of a member each distinct from the other but sufficiently spaced in conjunction with the action of the piston carried abutment member to achieve the desired end. Also whilst reference is made herein to the helical abutment feature being about the axis of the barrel and/or piston, persons skilled in the art will appreciate how, if desired, it can be some offsetting from that axis while still achieving the end of providing a readily moveable and scale referenced adjustment whereby there can be control of the discharging quantity.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION OF THE INVENTION

Preferred forms of the present invention will now be described with reference to the accompanying drawings in which;

FIG. 1 shows a preferred drench gun in accordance with the present invention with its squeezable handle in its biassed apart condition which it assumes at the end of the withdrawal of the piston in the barrel under the action of a spring within the handle structure, there being positioned adjacent the handle, for easy adjustment, a rotatable member adapted to adjust the position of the internal abutment member which is to coact at the end of the dispensing stroke with a step of the appropriate helical abutment feature, FIG. 2 is a top view of the arrangement of FIG. 1, FIG. 3 is an outlet end elevation of the member of FIG. 1, FIG. 4 is an elevational view of the intake end view of the dispenser of FIG. 1, FIG. 5 is an exploded view of the apparatus of FIGS. 1 through 4 showing the rotatable member and the to be carried abutment member thereof which is to abut the preferred helical staircase arrangement to be described hereafter, the exploded view of FIG. 5 showing the provision of two one way valve arrangements, one on the outlet side of the barrel and the other in or on the piston or at least the carried conduit thereof, FIG. 6A is a side elevational section of the apparatus of the drawings in its fully withdrawn condition under the action of a spring, FIG. 6B is the same as FIG. 6A but showing the piston at the end of its discharging movement within the barrel, the piston as an assembly including a piston proper and a carried conduit with its one way valve arrangement, FIG. 7A shows in perspective a cut away view of the apparatus as in FIG. 6A, FIG. 7B shows a cut away view in perspective of the apparatus as it is in FIG. 6B, FIGS. 8A through 8F shows different views of a moulded component adapted to be fabricated in and/or adjacent the barrel member shown in FIG. 5 and held thereto by appropriate arrangements such as to present a helical staircase as the helical abutment feature to limit the stroke of the piston assembly, FIGS. 9A through 9E show the helical abutment features of FIGS. 15A through 15E and a corresponding relationship between the outletted barrel and the helical abutment feature, FIG. 10 shows another preferred form of the drench gun similar to that as depicted in FIG. 1 but including a handle pressure adjustment feature (as disclosed in our NZ Patent Specification No.505468/508217 and NZ Registered Design No.400572) as well as a mounting hook FIG. 11 is a top view of the arrangement of FIG. 10, FIG. 12 is an outlet end elevation of the member of FIG. 10, FIG. 13 is an elevational view of the intake end view of the dispenser of FIG. 10, FIG. 14 is an exploded view of the apparatus of FIGS. 10 through 13 showing the rotatable member, and another preferred form of the helical staircase arrangement to be described hereafter, this view being similar to that of FIG. 5, FIG. 15A is similar to FIG. 6A but in respect of the embodiment of FIGS. 10 to 14, FIG. 15B is similar to FIG. 15A showing the piston at the end of its discharging movement within the barrel, the piston as an assembly including a piston proper and a carried conduit with its one way valve arrangement, FIG. 16 shows in perspective a cut away view of the apparatus as in FIG. 15A, and FIGS. 17A through 17F shows different views of one form of staircase moulded component shown as "A" in FIG. 14.

FIG. 18A show the barrel and escarpment member or staircase member.

FIG. 18B shows the barrel and escarpment member or staircase member as in FIG. 18A as mated.

Figure 4:
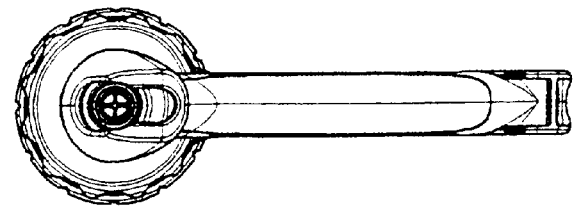
Figure 2:
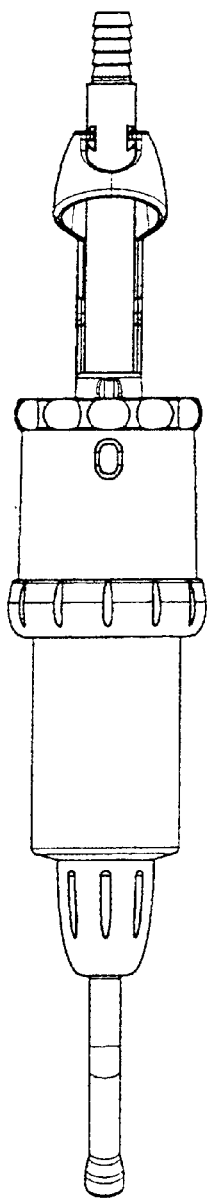

Preferred forms of the present invention are preferably made using where possible moulded plastic components e.g., of suitable injection moulded plastics, such as, a polycarbonate from a transparent barrel.

Of course usual seal type materials are utilised about the piston (e.g., a silicone rubber) such as those as used in such prior art devices previously referred to.

In one preferred form of the present invention where possible a majority of the components are moulded in an appropriate plastics material. If desired however, metal members can be used for those likely to be subjected to abuse and requiring a degree of malleability.

In the arrangement as shown the assembly comprises a barrel component 1 having an outlet 2 and an end 3 adapted to receive the assemblage 4 of the piston assembly. The outlet end 2 is adapted to be associated with a one way valve assembly 5 (preferably such one way valves including a sprung shuttle that seats and unseats from the associated member) which directs discharging material out of an appropriate outlet member 6.

As can be seen the helical abutment feature 7 is held in a condition as shown in FIGS. 9A through 9E in a fixed relationship with the barrel member 1 (for clarity FIGS. 9A through 9E not showing any threading on the outlet spigot 2). The arrangement is held in position by association of the member 8 and its thread 9 to the collar 10. This collar 10 holds certain of the components together in much the same way as member 11 holds the outlet member 12 in a fixed relationship to the member 2 with the one way valve assemblies 5 there between.

Figure 1:
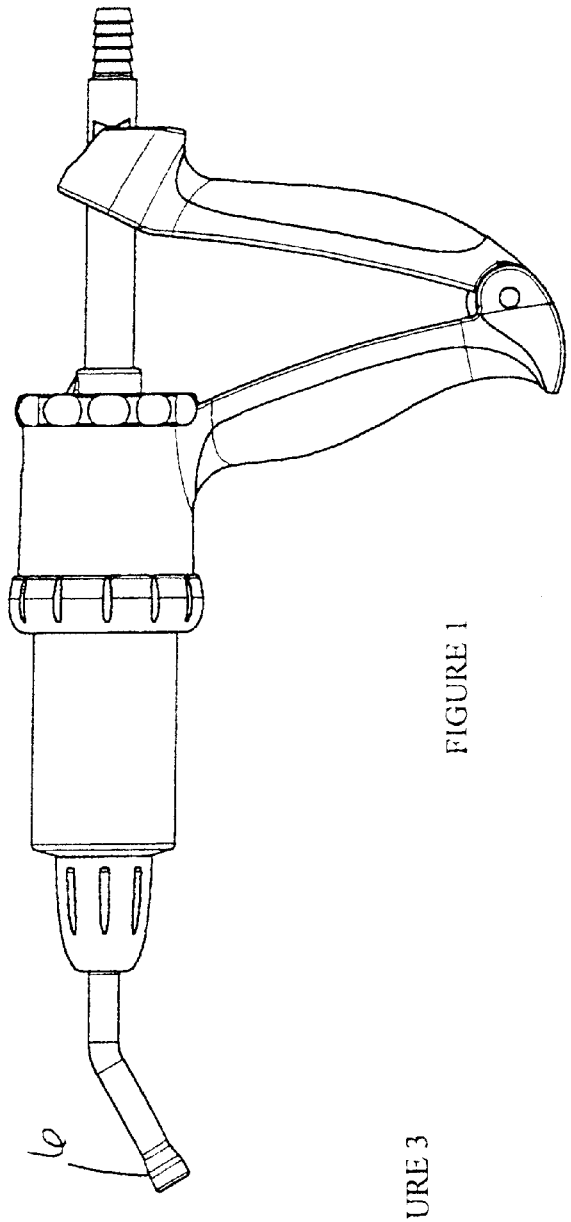
Figure 3:
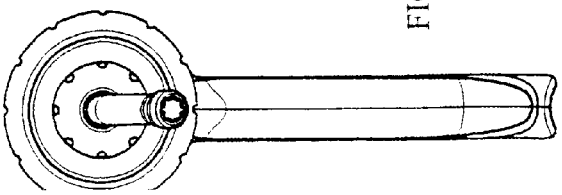
Figure 5:
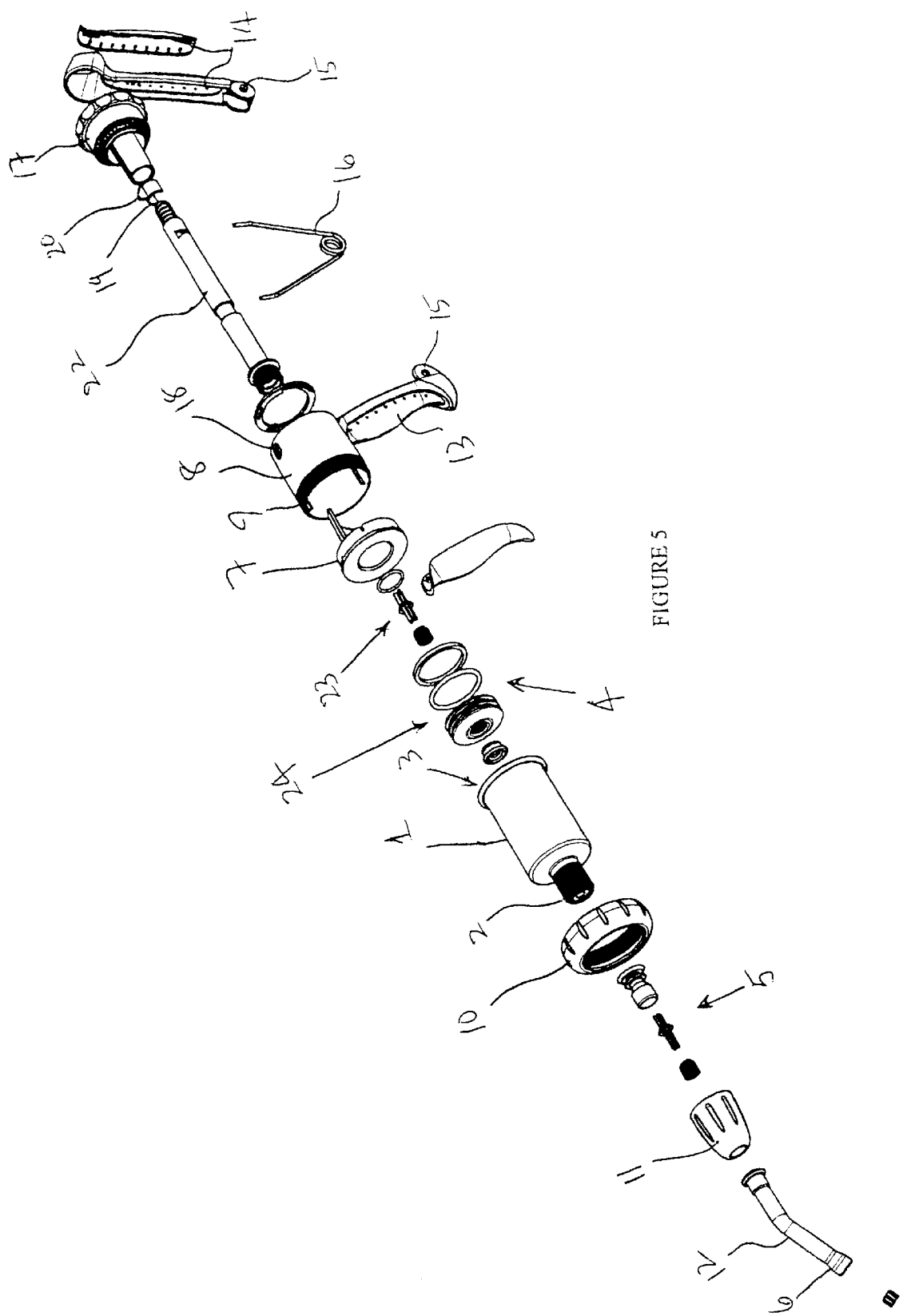

The member 8 carries a first part 13 of the handle structure with the other component of the handle structure 14 pivoted thereto at the axis 15 (or to be pivoted at the axis 15) which preferably locates the biassing spring 16 which has the effect of opening the handle members to the condition shown in FIG. 1.

The abutment member to be adjustable by the operator includes the arrangement 17 which is rotatable so as to present an indication of the quantity to be dispensed via a window 18. The member 17 however carries the member 19 with its abutment shoulder 20 which will act on one step only of the spiral or helical staircase of the member shown in FIGS. 8A through 8F. In those figures can be seen the multiple steps 21.

Carried by the piston assembly in addition to the components 17, 19 and 20 is the conduit 22 and the one way valve assembly or assemblage 23 fixed by appropriate means at the end of the piston proper provided by the piston defining assembly or assemblage 24.

Figure 7A:
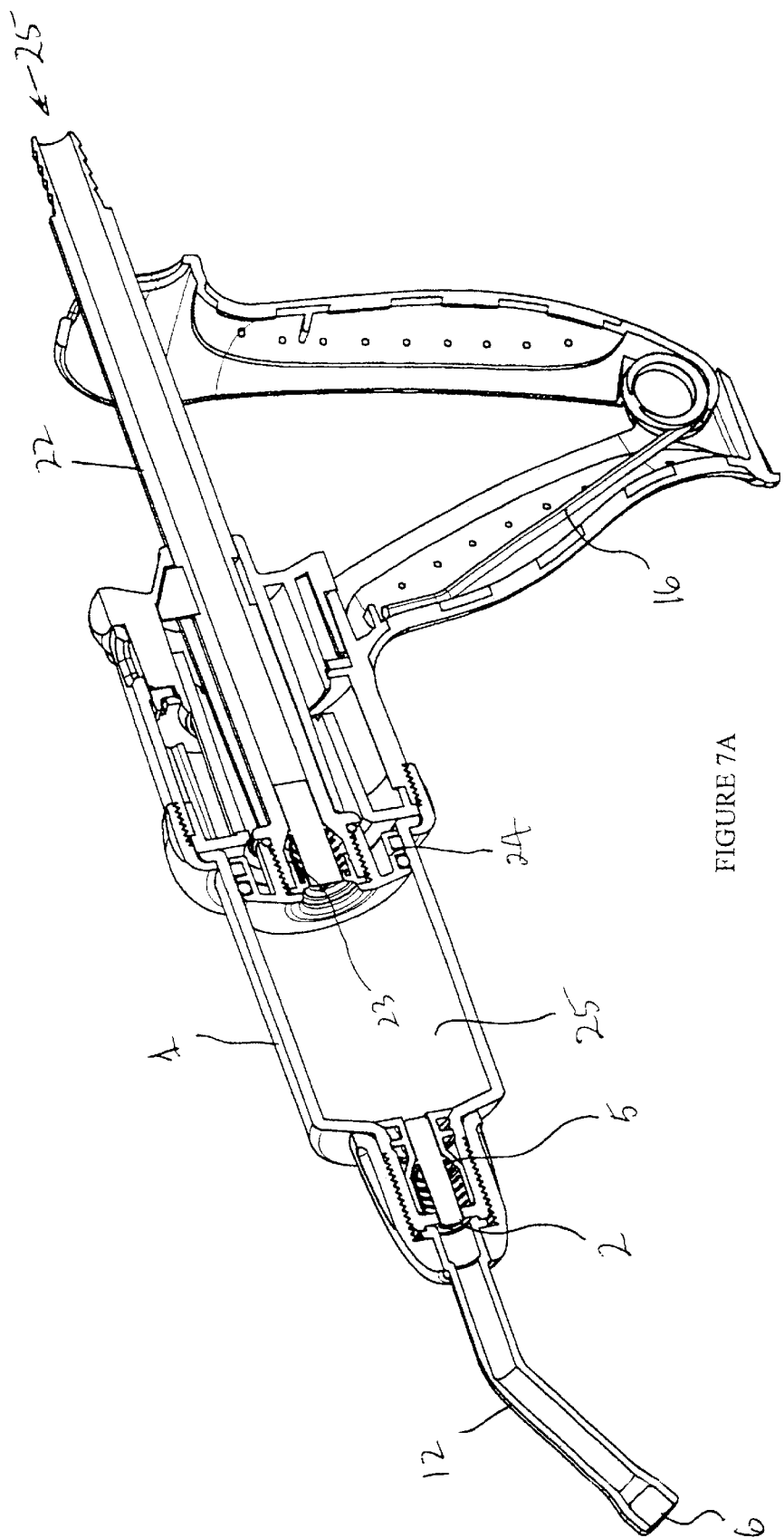
Figure 7B:
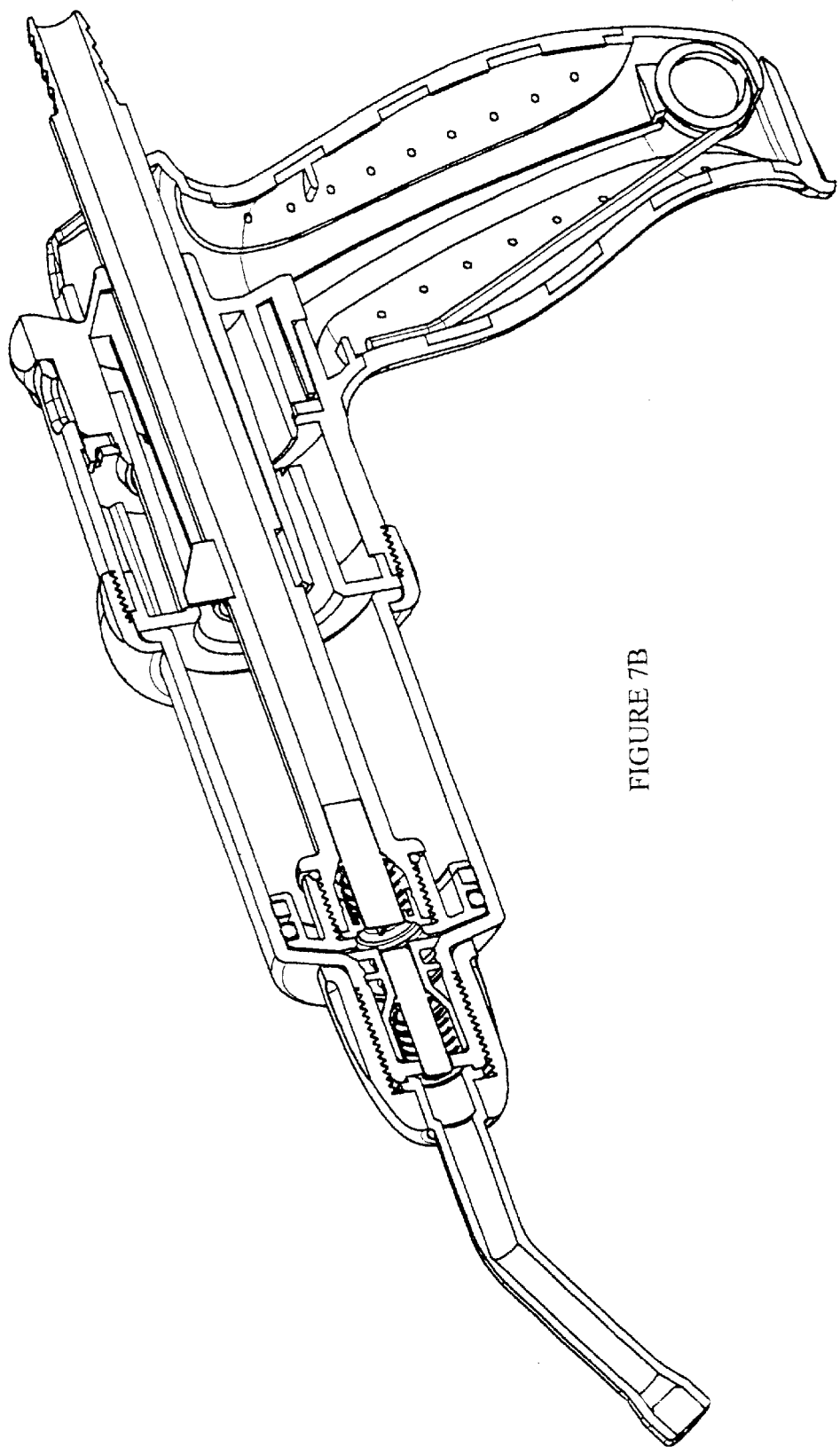
Figure 8D:
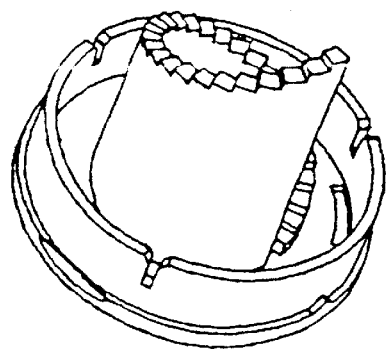
Figure 8C:
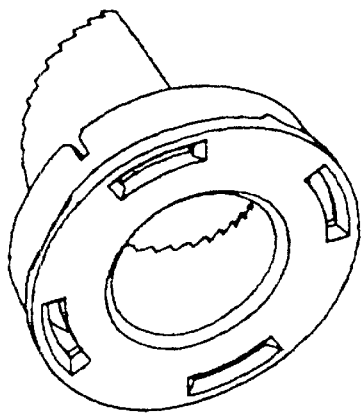
Figure 8E:
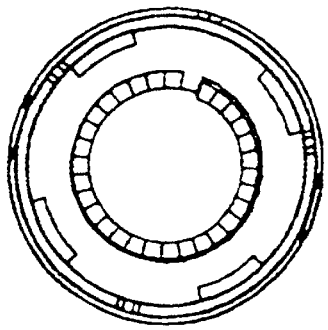
Figure 8A:
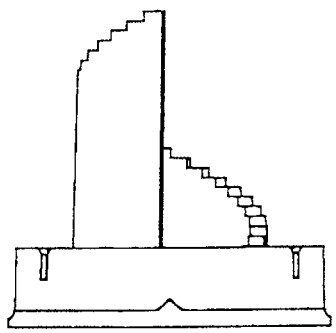
Figure 8B:
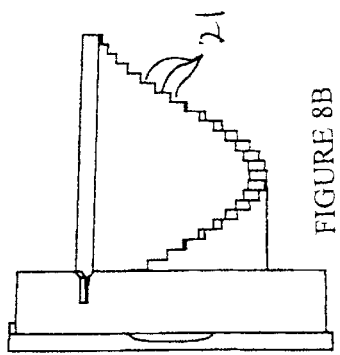
Figure 8F:
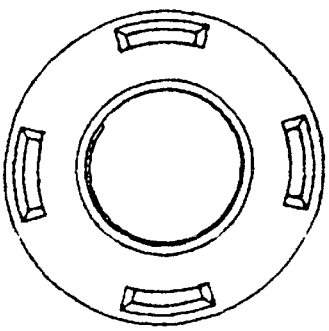
Figure 14:
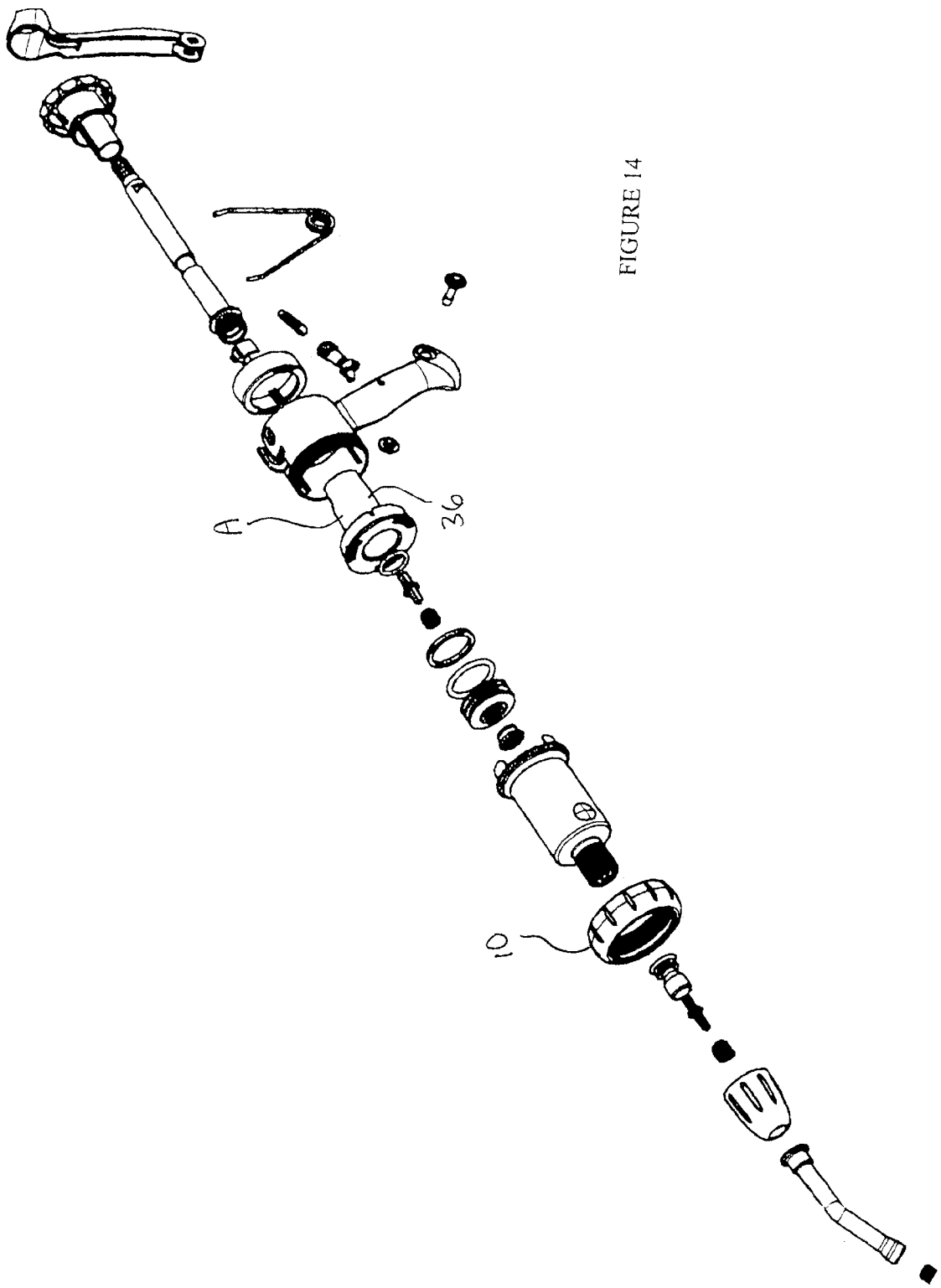
Figure 15A:
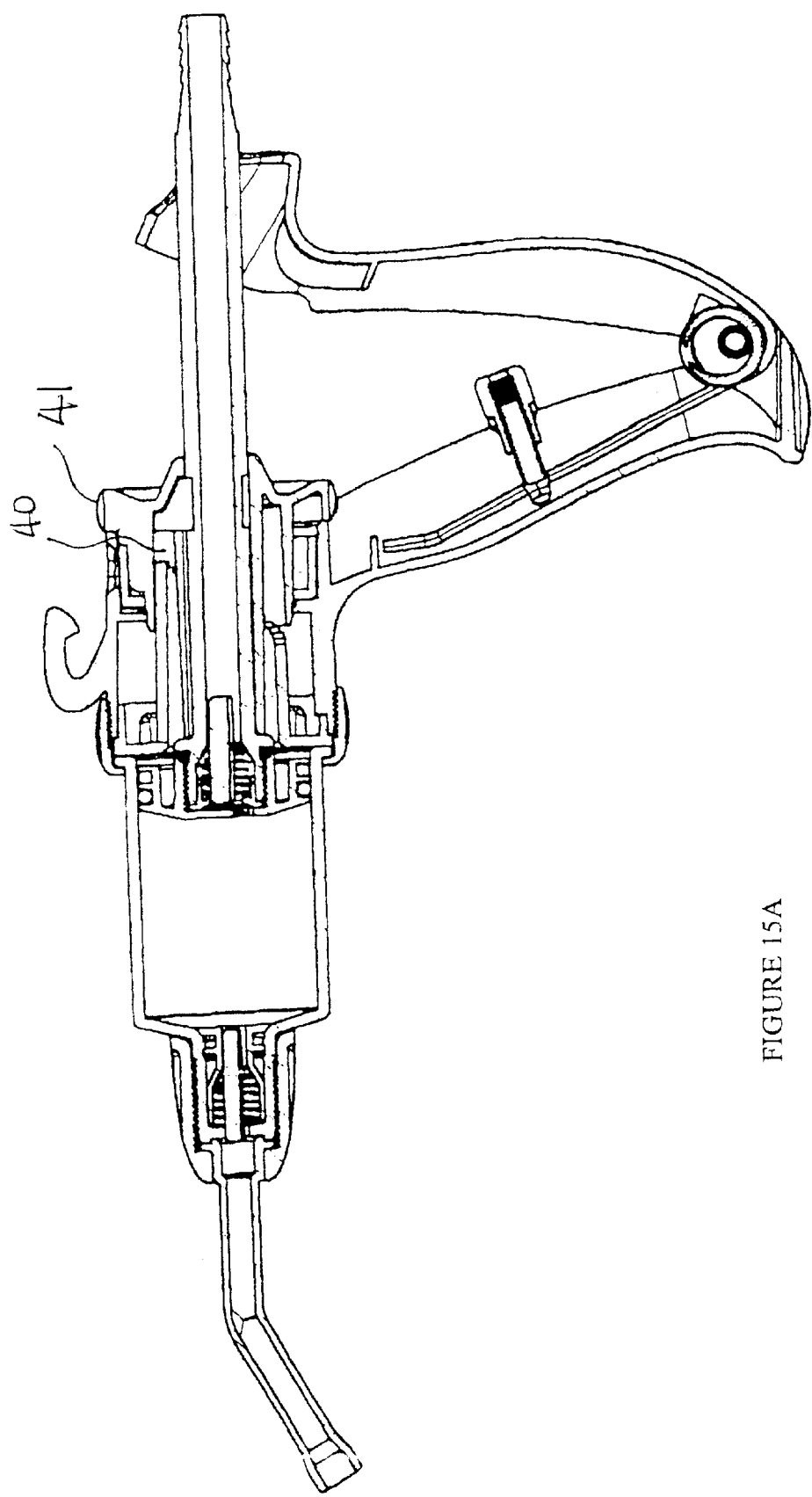
Figure 15B:
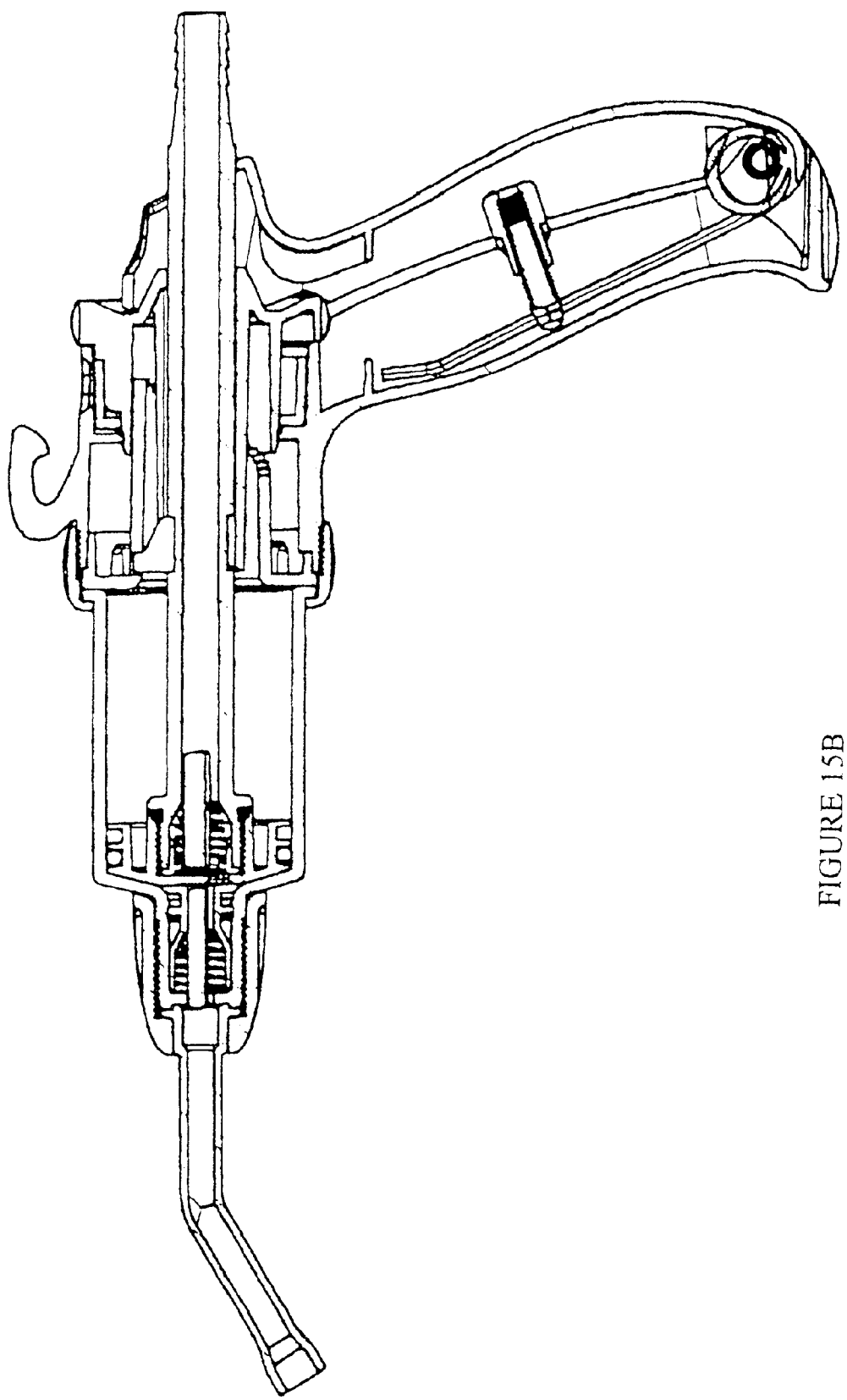
Figure 16:
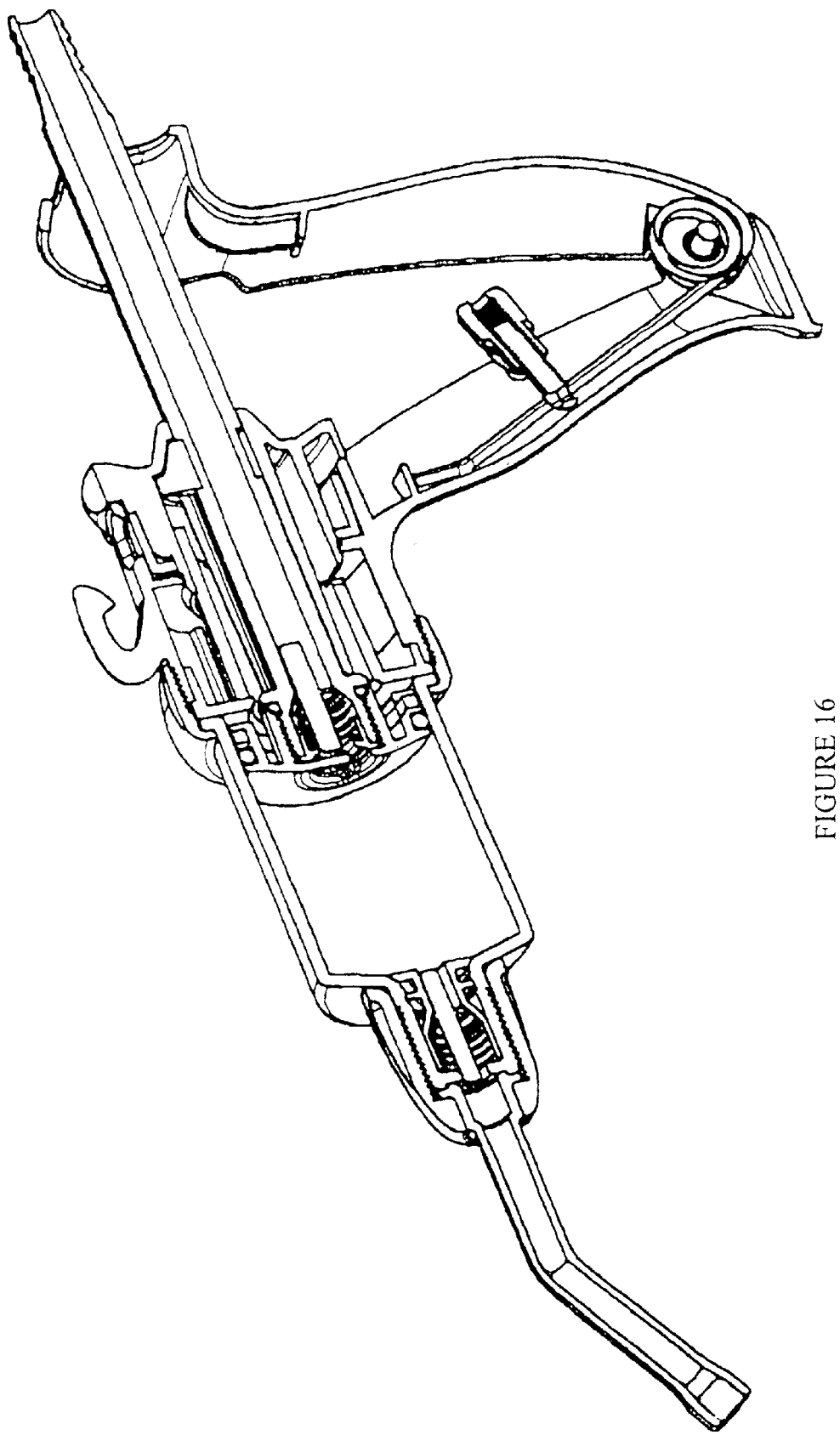

Persons skilled in the art, by reference to the detailed and clear drawings filed herewith, will see the manner by which liquid entering from, for example, inlet 25 can pass via the one way valve assembly 23 of the piston proper 24 as the gun moves from the condition shown in FIG. 7B under the action of the spring back to the condition shown in FIG. 7A. In so doing liquid having entered the conduit 22 via the inlet 25 enters the barrel chamber 25 to be subsequently discharged therefrom upon squeezing of the handle assembly via the outlet 2 and the one way valve assembly 5 to subsequently exit out of the outlet 6.

One way valve arrangements allow accordingly movement of liquids during sequential dispensing actions in the direction from the right to the left with respect of FIG. 7A.

Figure 6A:
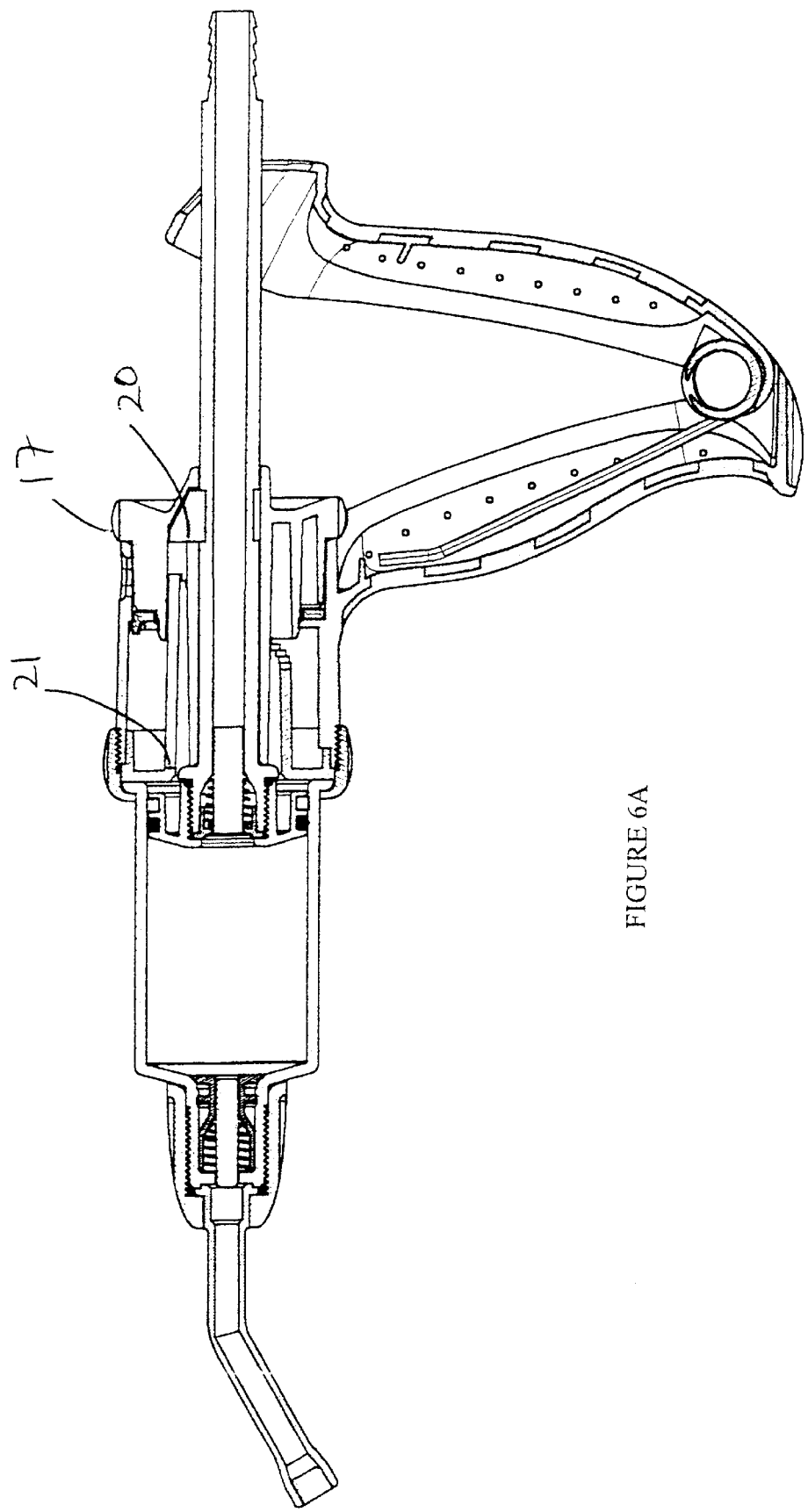
Figure 6B:
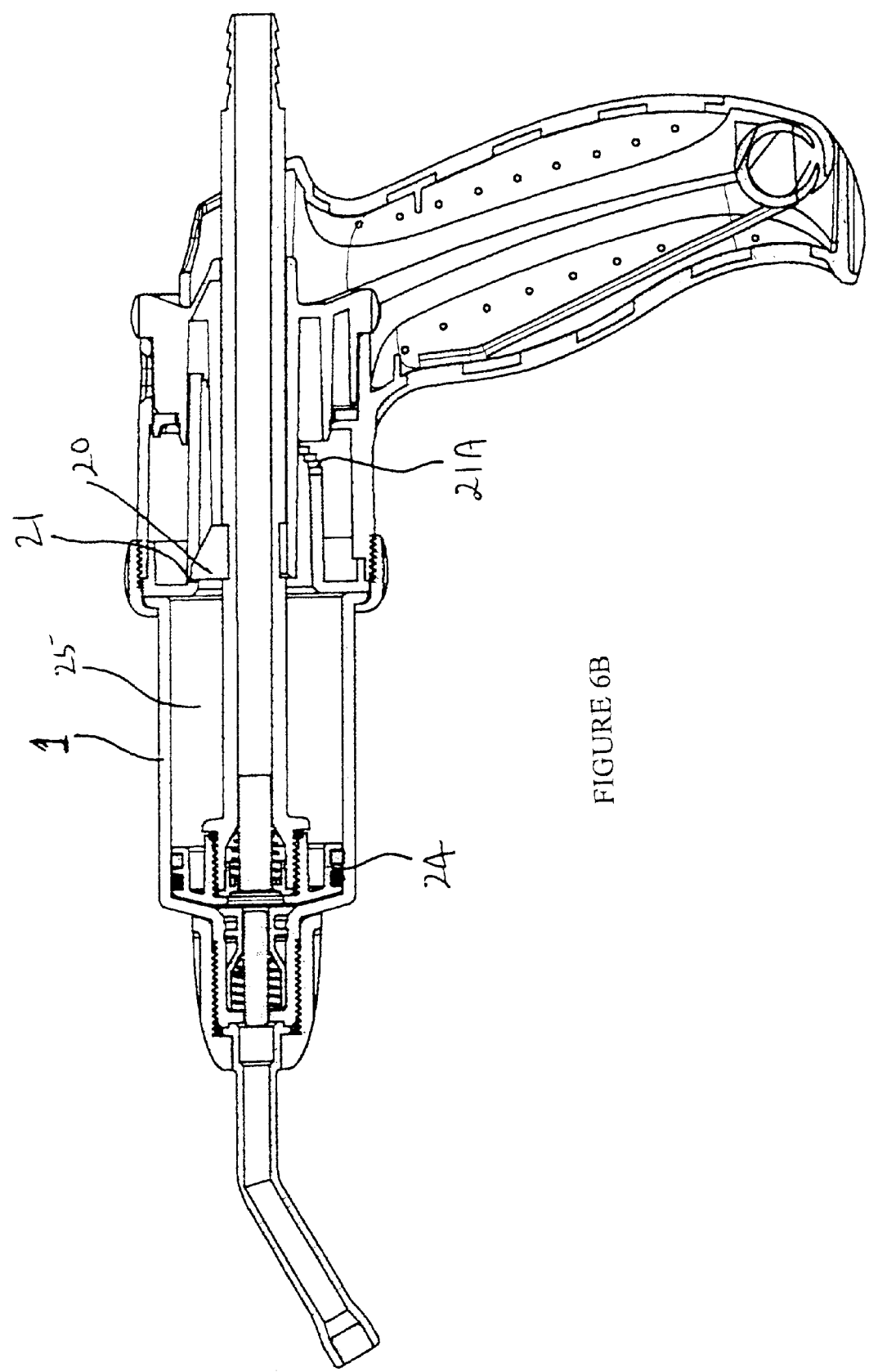

To adjust the stroke, (ie; the limits of reciprocal movement between the condition shown in FIGS. 7A and 7B) the dispensing volume of the chamber 5 is adjusted by appropriate indexing or reference of the member 20 to a particular step 21 of the gun. In use (as best can be seen in FIGS. 6A and 6B) the member 7 does not move relative to the barrel 1 during any such adjustment and nor during any such dispensing action.

The effect of rotation of the member 17 is simply to align the abutment member 20 onto the appropriate step 21 thereby to control volume. In FIGS. 6A and 6B the lower most step 21 has been chosen thereby to maximise the quantity to be dispensed. Any of the higher steps 21 in the staircase feature could instead have been utilised thereby achieving a kind of abutment as shown in FIG. 6B with the piston member proper 24 having travelled less to the left within the chamber 25 of the barrel 1.

Another preferred form of the present invention is that shown in FIGS. 10 through 17 F.

This form of the invention as can be seen includes different moulded components in many ways from that previously described in respect of FIGS. 1 to 9. Apparent is the feature 26 which enables rotational adjustment of a knob which will affect the spring pressure and thus the bias rearwardly of the part 27 of the handle assembly 28. Of course it is that component 29 of the handle pivoted at 30 to component 27 that locates the spring the tension of which is being adjusted by the member 26 in a manner as disclosed in our NZ Patent Specification No.505468/508217 the full content of which is hereby included by way of reference.

Another aspect readily apparent from say FIG. 10 is the sleeve member 31 of the handle component 29 also including a mounting hook 32.

Also apparent is the fact that the component 33 which defines the barrel within which the piston moves includes a retention screw cap 34 for mounting the outlet nozzle 35 into a fluid conjunction with the outletted barrel 33 with its one way valve.

Within the exploded assembly of the embodiment as shown is FIGS. 10 through 13 there is the component "A" designated 36 (which preferably is of the form shown in FIGS. 17A through 17F). It can be seen that this component 36 includes the staircase feature 37 as well as a more axially extending region 37.

It can also be said that the cylindrical region 38 which is to be received within the sleeve 31 includes recesses 39 to index into position with respect to complimentary components within the sleeve 31 thus fixing the position thereof so that the only variable for dose is the rotation of the abutment member 40 (see FIG. 15A) carried about and rotatably adjustable by the member 41.

If one considers a variation of the staircase abutment features as shown in each of FIGS. 8A through 8F as being interchangeable with that of FIGS. 17A through 17F the component of figures of 8A through 8F controls the dispensing stroke over a wider range of possibilities up to for example 70 milliliters whilst that of FIGS. 17A through 17F does not have that possibility of up to 70 milliliters. Instead by cessation of the staircase prior to its full spiral extending to the point 42 those dispensing strokes consistent with say from 50 through to 70 milliliters are not possible. Thus the variant as shown in FIGS. 8A through 8F should be considered as providing incremented dosages out to 70 milliliters whilst that of 17A through 17F provide dispensing stroke limited dosages out to only 50 milliliters. For many medicaments some limitation to avoid accidental overdose may be desirable and thus the present invention provides for the prospect for the range of components that may be interchanged to limit the maximum dosage. Of course variations are possible that also limit the minimum doseage available and the lower most step of each of the components of FIGS. 8A through 8F and 17A through 17F likewise can be selective as to the minimum doseage to be dispensed.

A feature of the present invention is the prospect of interchangeability and in this respect we refer to a preferred interchangeability of one or both of the barrel and the piston in addition to or as well as any interchangeability of the escarpment and/or spiral staircase member. In accompanying FIGS. 18A and 18B we show how a moulded barrel defining member can index into a complementary escarpment member or staircase member using a male into female inter-engagement or vice versa. Such indexing is desirable as it makes more easy the correct retention of the barrel reliant upon the screw threaded component 10 of FIG. 5 or FIG. 14 and of course can be used to ensure a correct barrel is associated with the correct and intended escarpment member only.

In FIG. 18A it can be seen that the member 36 and the barrel 43 with its threaded outlet end 44 for engagement to an outletting assembly (but preferably with the one way valve internally of the region 14) can have its male protuberances 45 received into corresponding openings 46 of the member 36. The member 36 includes a shoulder 47 adapted to butt against the end of the sleeve 8 or 31 whilst the shoulder 48 of the flange of the member 43 is adapted to be captured by the screw fittable collar 10 which is to engage a screw thread of the member 31 shown as 9 in FIG. 5.

The arrangement therefore of FIG. 18B is simply of the indexed components with their fixing being reliant upon the screwing home of the collar 10.

Figure 19A:
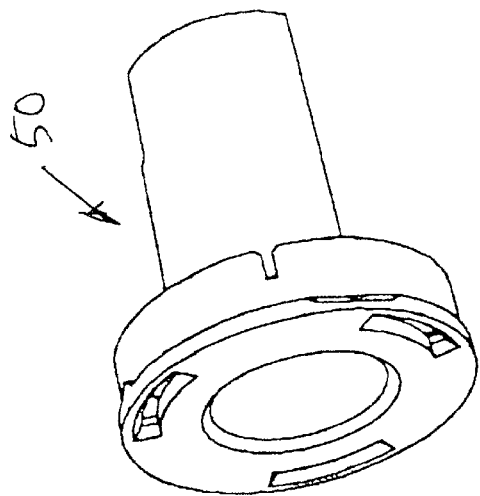
FIG. 19A is similar to FIG. 18A but with different sized barrel and escarpment member.
Figure 19B:
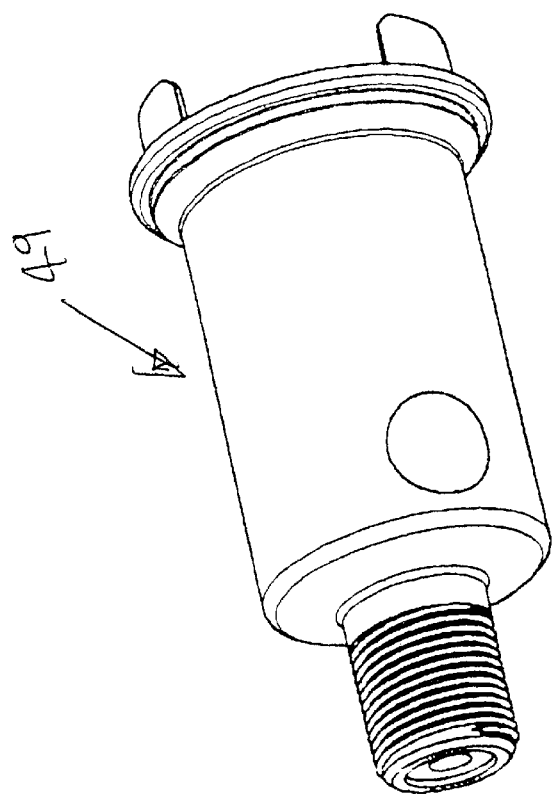
FIG. 19B shows the barrel and escarpment member of FIG. 19A as mated.
Figure 19B:
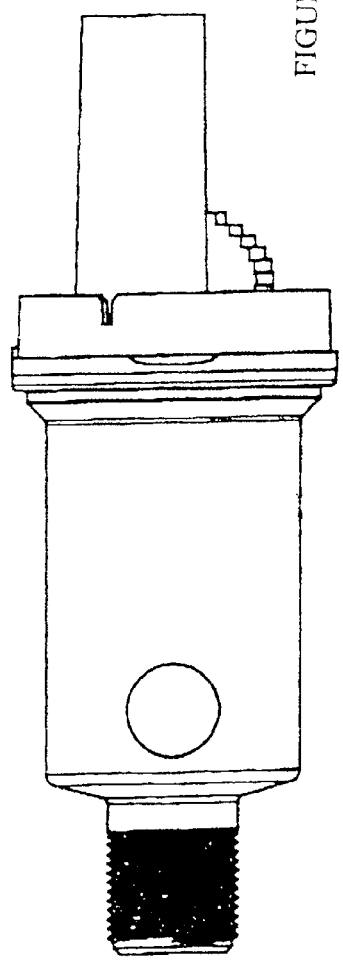

As can been seen however interchangeability can occur and in FIGS. 19A and 19B a different barrel 49 can be provided which may require a different piston member to correspond to that changed barrel to be engaged to the conduit 22.

In the particular arrangement of FIGS. 19A and 19B a different indexing male/female arrangement is provided to ensure that the escarpment member 50 is only used with the barrel member 49 although in other forms of the present invention there can be the prospect of interchangeability where a barrel 49 might be engageable with an escarpment member such as 36 but where there is in indexability of the male into female components.

It can been seen therefore that with such a prospect of disassembly and reassembly in a variety of different configurations. As a consequence the dosage flexibility is expanded beyond that which can be achieved simply reliant upon the stroke limiting with a single spiral staircase type arrangement.

Other variations include the prospect of a longer piston member as well for a same barrel and a same escarpment member. For simplicity however and to cover a significant range of options it is intended that the apparatus be offered with two or more barrel and escarpment member sets each barrel being dedicated to one of the escarpment members such that simply instructions can indicate to a farmer or the like just what combination should be utilised to provide what dose range and so that the dosages provided by each incremental step are also capable of being tabled.

Persons skilled in the art will appreciate therefore how the present invention provides an alternative to other adjustment features in dispensing guns.

I claim:

1. Dispensing apparatus comprising:
    a barrel with an inlet and an outlet and an operator actuable piston reciprocally movable in said barrel,
    said piston, in use, when moving away from said outlet, allowing a liquid to enter space between said piston and said outlet,
    and subsequent discharging movement of said piston, in use, towards said outlet causes liquid to exit said outlet,
    and a stroke of said discharging movement being controlled by a stop mechanism for the piston, said stop mechanism including a spiral staircase member through which liquid can pass and a staircase step abutment member carried by one of the piston and an assembly, which includes the piston, butting at the limit of said discharging movement on a step of said spiral staircase member, said abutment member being rotatable about both the barrel and spiral staircase member axes by externally accessible means to determine a stroke limiting choice of a step in the staircase to encounter the abutment member and thus the quantity of liquid to be dispensed by a single discharging movement of said piston.

2. Apparatus of claim 1 wherein said barrel is detachable.

3. Apparatus of claim 1 wherein at least one of the barrel, piston and helical abutment structure is detachable.

4. Liquid dispensing apparatus comprising: hand actuable means to move a piston against a bias force so as to discharge at least part of liquid content from a barrel, said barrel having fixed relative thereto a helical abutment structure and said piston forming part of an assembly which allows an uptake of liquid into said barrel during retraction under the action of said bias force to complete part of a liquid uptake step and a subsequent liquid discharging step, all passing through the barrel, and wherein a limit of the liquid discharging step from a retracted piston condition is determined by selection of a part of the helical abutment structure to be encountered during the discharging step.

5. Apparatus of claim 4 wherein said helical abutment structure is a staircase.

6. Apparatus of claim 4 wherein said helical abutment structure is a continuous surface.

7. In a drench gun being actuated to cause a piston to reciprocate within a dispensing barrel, there being a one way valve to allow an uptake of liquid to be dispensed into a dispensing side of the piston in the barrel,
    a stroke adjustment mechanism including
        an abutment member carried by the piston capable of being rotated about a piston axis by an adjustment accessible to an operator, and
        a helical abutment feature adapted to provide an abutment for said rotatable abutment member thereby to adjust the allowed extent of travel of the piston during a dispensing motion owing to an end of travel occurrence of an abutment between the piston carried abutment member and the helical abutment feature for passage of liquid through the barrel.

8. Apparatus of claim 7 wherein said helical abutment feature is a moulded element fixed in a fabricated structure relative to the barrel.

9. Apparatus of claim 7 wherein said helical abutment feature defines a spiral staircase.

10. Apparatus of claim 7 wherein said piston includes an axial conduit controlled by said one way valve.

11. Apparatus of claim 7 wherein said piston is biassed to a retracted condition.

12. Apparatus of claim 11 wherein said piston is biassed by the handle structure.

13. Apparatus of claim 12 wherein the handle is squeezed against a bias force to cause a liquid dispensing stroke.

14. Apparatus of claim 7 wherein at least one of the barrel, the piston and the helical abutment feature is removable.

15. Apparatus for dispensing a selected volume of a liquid, said apparatus comprising:
    a handle assembly of pivotally interconnected first and second handle components biased apart about a pivot, one of said components at a region distal from said pivot having a sleeve form, an axis of the sleeve form extending normal to said pivot axis,
    a piston assembly linked from the second handle component from a region distal thereof from said pivot, the piston assembly extending through said sleeve, said piston assembly connecting said second component to a piston and defining a conduit for receiving and conveying liquid to be dispensed via a one way valve out of said piston,
    an abutment defining member of said piston assembly being rotatable about a stroke axis thereof by manual actuation externally of said sleeve,
    an escarpment member located at least in part in said sleeve and providing an escarpment of steps on each of at least several of which part of said abutment defining member can abut to limit a discharge stroke of said piston assembly upon a manual squeezing of the handle components together about the pivot, and a barrel member about the piston held in a fixed relationship with both the sleeve and the escarpment member, said barrel member having an outlet, wherein liquid can enter said barrel between said piston and outlet at least as said second handle component retracts under the action of said bias and thereafter the piston can drive liquid through the barrel to the extent allowed by the discharge stroke limit of the piston in the barrel as the handle components are squeezed against the bias, the stroke limit being determined by a particular alignment of the abutment defining member with a particular step of the escarpment member.

16. Apparatus as claimed in claim 15 wherein said barrel member is held in said fixed relationship with the sleeve and escarpment member by a screw engaged collar engaged to said sleeve.

17. Apparatus of claim 15 wherein said barrel member indexes to said escarpment member by a male/female inter-engagement.

18. Apparatus as claimed in claim 17 wherein said escarpment member is in the form of a spiral staircase formed as part of a moulded member having an outwardly extending flange to butt on one end of said sleeve of said first component and an inwardly extending flange having openings each to receive a projection of said barrel in said male/female indexing manner.

19. Apparatus for dispensing a selected volume of a liquid, said apparatus comprising
   a handle assembly of first and second handle components inter-related to ensure reproducible movement towards and away from each other,
   an assembly supported on one of said handle components, the assembly including
      an escarpment member having a spiral staircase facing towards the second handle component and
      a barrel coaxially aligned with said escarpment member, said barrel having an outlet, and
   a conduit capable of being connected to a source of liquid supply which extends from said second handle component into said barrel where the conduit carries a piston to enable liquid entry into the barrel upon retraction of the piston,
   and wherein the conduit carries there around an abutment member associated with an external rotational control which can be aligned with a desired step of the escarpment member spiral staircase so as to be determinate of the dispensing stroke limit of the piston and amount of passage of liquid through the barrel.

20. Apparatus for dispensing a selected volume of a liquid, said apparatus comprising:
   a handle assembly of pivotally interconnected first and second handle components biassed apart about a pivot, one of said components at a region distal from said pivot having a sleeve form, the axis of the sleeve form extending normal to an axis of said pivot;
   a piston assembly linked from the second handle component extending through said sleeve, said piston assembly connecting said second component to an interchangeable piston and defining a conduit for the receiving and conveying therethrough of liquid to be dispensed via a one way valve out of said piston;
   an abutment defining member rotatable about a stroke axis by manual actuation externally of said sleeve;
   an interchangeable escarpment member located at least in part in said sleeve and providing an escarpment of steps on each of at least of several of which part of said abutment defining member can abut to limit a discharge stroke of said piston assembly upon a manual squeezing of the handle components together about the pivot; and
   an interchangeable barrel member bout the piston held in a fixed relationship with both the sleeve and the escarpment member, said barrel member having an outlet extending to a one way valved outlet assembly;
   wherein liquid can enter said barrel between said piston and outlet at least as said second handle component retracts under the action of said bias and thereafter the piston can drive liquid through the barrel to the extent allowed by the discharge stroke limit of the piston in the barrel as the handle components are squeezed against the bias, the stroke limit being determined by a particular alignment of the abutment defining member with a particular step of the escarpment member,
   and wherein interchange of at least one of the interchangeable members can vary the range of volumes capable of being dispensed.

21. Apparatus of claim 20 wherein both the piston and its barrel is interchangeable.

22. Apparatus for dispensing a selected volume of a liquid, said apparatus comprising
   a handle assembly of first and second handle components inter-related to ensure reproducible movement towards and away from each other;
   an assembly supported by one of said handle components which includes an interchangeable barrel having an outlet; and
   a conduit capable of being connected to a source of liquid supply which extends from said second handle component into said barrel where it carries an interchangeable piston for the barrel, there being a one way valve in at least one of the conduit and the piston to enable liquid entry and passage therethrough upon retraction of the piston; and
   an interacting arrangement of an abutment member and an escarpment member capable of being interactive to limit a stroke of said piston in said barrel, yet by rotation of the members relative to each other can vary that stroke;
   and wherein a volume of the liquid is varied by at least one of
      (a) barrel interchange,
      (b) piston interchange,
      (c) escarpment member interchange, and
      (d) abutment member interchange.

23. Apparatus of claim 22 wherein, in use, said apparatus can dispense incrementally over a fist range and, after reassembly with associated components, can dispense incrementally over a second range not coextensive with said first range.

24. In combination (I) apparatus for dispensing a selected volume of a liquid, said apparatus including:
   a handle assembly of pivotally interconnected first and second handle components biassed apart about a pivot, one of said components at a region distal from said pivot having a sleeve form, an axis of the sleeve form extending normal to said pivot axis;
   a piston assembly linked from the second handle component extending through said sleeve, said piston assembly connecting said second component to an interchangeable piston and defining a conduit for the receiving and conveying therethrough of liquid to be dispensed via a one way valve out of said piston;

an abutment defining member rotatable about a stroke axis by manual actuation externally of said sleeve;

an interchangeable escarpment member located at least in part in said sleeve and providing an escarpment of steps on each of at least of several of which part of said abutment defining member can abut to limit a discharge stroke of said piston assembly upon a manual squeezing of the handle components together about the pivot; and an interchangeable barrel member about the piston held in a fixed relationship with both the sleeve and the escarpment member, said barrel member having an outlet extending to a one way valved outlet assembly;

wherein liquid can enter said barrel between said piston and outlet at least as said second handle component retracts under the action of said bias and thereafter the piston can drive liquid through the barrel to the extent allowed by the discharge stroke limit of the piston in the barrel as the handle components are squeezed against the bias, the stroke limit being determined by a particular alignment of the abutment defining member with a particular step of the escarpment member, and wherein interchange of at least one of the interchangeable members can vary the range of volumes capable of being dispensed, and (II) at least one of said interchangeable members the use of which in the apparatus will lead to a dosage range not coextensive with the dosage range of the apparatus in its initial form.

25. In combination, (I) apparatus for dispensing a selected volume of a liquid said apparatus including a handle assembly of first and second handle components inter-related to ensure reproducible movement towards and away from each other;

an assembly supported by one of said handle components which includes an interchangeable barrel having an outlet; and a conduit capable of being connected to a source of liquid supply which extends from said second handle component into said barrel where it carries an interchangeable piston for the barrel, there being a one way valve in at least one of the conduit and the piston to enable liquid entry and passage therethrough upon retraction of the piston; and an interacting arrangement of an abutment member and an escarpment member capable of being interactive to limit a stroke of said piston in said barrel, yet by rotation of the members relative to each other can vary that stroke;

and wherein a volume of the liquid is varied by at least one of
(a) barrel interchange,
(b) piston interchange,
(c) escarpment member interchange, and
(d) abutment member interchange, and (II) at least one additional component to allow at least one of barrel interchange, piston interchange, escarpment member interchange and abutment member interchange.

26. A method of varying a range of incremental dosages capable of being dispensed from a dispensing apparatus which comprises (A) taking a combination of
(I) apparatus including a handle assembly of first and second handle components inter-related to ensure reproducible movement towards and away from each other;

an assembly supported by one of said handle components which includes an interchangeable barrel having an outlet; and a conduit capable of being connected to a source of liquid supply which extends from said second handle component into said barrel where it carries an interchangeable piston for the barrel, there being a one way valve in at least one of the conduit and the piston to enable liquid entry and passage therethrough upon retraction of the piston; and an interacting arrangement of an abutment member and an escarpment member capable of being interactive to limit a stroke of said piston in said barrel, yet by rotation of the members relative to each other can vary that stroke;

and wherein a volume of the liquid is varied by at least one of
(a) barrel interchange,
(b) piston interchange, and
(c) escarpment member interchange (II) at least one additional component to allow at least one of barrel interchange, piston interchange and escarpment member interchange, and (B) varying the discharge volume allowed for a particular stroke limit by component interchange selected from at least one of barrel interchange, piston interchange and escarpment member interchange.

27. Apparatus suitable for dispensing a selected volume of a liquid, said apparatus comprising:

a first handle component, a second handle component mounted to the first handle component so that the handle components can be squeezed reproducibly towards each other, a biassing mechanism adapted to bias the handle components, a barrel proximally supported by the first handle component, said barrel having distally a discharge outlet, a ported piston reciprocally movable within said barrel on a stroke axis in both a discharge advance direction towards the barrel outlet and a recharge retract direction, a conduit of the piston located at one end thereof so that both the piston and conduit are movable together relative to both the barrel and the first handle component under the action of the second handle component to which the conduit is engaged, an end region of the conduit being adapted as an inlet for a feed supply of the liquid to be dispensed, a one way valve in at least one of the conduit and the ported piston to enable a net one way flow through both the conduit and piston of the liquid, in use, receivable via the inlet as the piston is being withdrawn in the barrel by the conduit under the action of the biassing mechanism, an abutment defining member located about and movable with the conduit, said abutment defining member being at an axial zone of the conduit at which it will remain as the conduit moves, yet the abutment defining member being rotatable about the conduit, an abutment defining member rotation control carried by the first handle component exteriorly in part accessible and capable of manual rotation thereby to control the rotational position of the abutment defining member about the conduit, and an escarpment member fixed against rotation relative to the barrel to define an escarpment of steps facing toward the handle components and surrounding the conduit between the piston and the abutment defining member, wherein depending on the rotational position of the abutment defining member about the conduit under the control of the rotatable control, a particular step in the escarpment of steps will determine the limit of a discharge stroke of said piston upon a manual squeezing towards each other of the first and second handle components against the return bias of the biassing mechanism, and wherein, in use, the retreat of the piston is to a retreated condition which is the same irrespective of the discharge stroke limiting step of the escarpment member aligned with the abutment defining member.

* * * * *